(12) United States Patent
Chen et al.

(10) Patent No.: US 10,071,955 B1
(45) Date of Patent: Sep. 11, 2018

(54) HIGH-YIELD CIRCULAR PRODUCTION METHOD OF TAURINE

(71) Applicant: QIANJIANG YONGAN PHARMACEUTICAL CO., LTD., Hubei Province (CN)

(72) Inventors: Yong Chen, Hubei Province (CN); Xiquan Fang, Hubei Province (CN); Shaobo Li, Hubei Province (CN)

(73) Assignee: QIANJIANG YONGAN PHARMACEUTICAL Co., Ltd., Hubei Province (CN)

( * ) Notice: Subject to any disclaimer, the term of this patent is extended or adjusted under 35 U.S.C. 154(b) by 0 days.

(21) Appl. No.: 15/678,737

(22) Filed: Aug. 16, 2017

(30) Foreign Application Priority Data

Jun. 16, 2017 (CN) .......................... 2017 1 0456576

(51) Int. Cl.
| | | |
|---|---|---|
| *C07C 309/00* | (2006.01) | |
| *C07C 303/02* | (2006.01) | |
| *C07C 303/22* | (2006.01) | |
| *B01D 15/36* | (2006.01) | |
| *B01J 49/53* | (2017.01) | |
| *B01J 27/232* | (2006.01) | |
| *C07C 303/44* | (2006.01) | |

(52) U.S. Cl.
CPC .......... *C07C 303/02* (2013.01); *B01D 15/362* (2013.01); *B01J 27/232* (2013.01); *B01J 49/53* (2017.01); *C07C 303/22* (2013.01); *C07C 303/44* (2013.01)

(58) Field of Classification Search
CPC ... C07C 303/02; C07C 303/44; C07C 303/22; B01J 49/53; B01J 27/232; B01D 15/362
See application file for complete search history.

(56) References Cited

U.S. PATENT DOCUMENTS 2,693,488 A * 11/1954 Sexton ..................... B01J 39/00
562/104

FOREIGN PATENT DOCUMENTS

CN          104513181        *   4/2015

OTHER PUBLICATIONS

CN104513181 translated (Year: 2015).*

* cited by examiner

*Primary Examiner* — Yevgeny Valenrod
*Assistant Examiner* — Blaine G Doletski
(74) *Attorney, Agent, or Firm* — Andrew W. Chu; Craft Chu PLLC

(57) ABSTRACT

The high-yield circular production method of taurine includes the following steps: S1, ethylene oxide reacts with sodium bisulfite solution to generate sodium hydroxyethyl sulfonate; S2, sodium hydroxyethyl sulfonate obtained in S1 is subjected to ammonolysis reaction in ammonia, and ammonia gas is recycled through flash evaporation upon completion of the reaction; S3, a reaction solution obtained after flash evaporation in S2 is sent to pass through an acidic cation exchange resin column, a material liquid containing taurine is collected, the inactivated resin column is subjected to regeneration with sulfur dioxide or carbon dioxide aqueous solution, and an eluent acquired during regeneration can be recycled directly or recycled after treated by sulfur dioxide; S4, the material liquid collected in S3 is subjected to post treatment to acquire taurine.

13 Claims, 2 Drawing Sheets

HIGH-YIELD CIRCULAR PRODUCTION METHOD OF TAURINE

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The invention belongs to the field of taurine preparation, and specifically refers to a high-yield circular production method of taurine.

2. Description of Related Art Including Information Disclosed Under 37 CFR 1.97 and 37 CFR 1.98

Taurine is a nonprotein amino acid; and as a medicine, it has functions of diminishing inflammation, relieving fever, easing pain, resisting convulsion, lowering blood pressure, etc., and is good for brain development, nerve conduction, perfection of visual functions and calcium absorption of infant. Taurine has a series unique function to cardiovascular system, and can strengthen human body and relieve tiredness; therefore, taurine has been gradually widely used in medical care, health food and other fields.

At present, more than 50000t taurine is prepared from derivative compounds of petroleum—ethylene oxide and monoethanolamine every year. So far, the majority of taurine is prepared from ethylene oxide after three steps: (1) ethylene oxide and sodium bisulfite are subjected to addition reaction to obtain sodium hydroxyethyl sulfonate; (2) sodium hydroxyethyl sulfonate is ammonolyzed to obtain sodium taurate; (3) an acid, such as hydrochloric acid, and preferably sulfuric acid is taken to implement neutral reaction to obtain taurine and an inorganic salt.

A method of synthesizing taurine from ethylene oxide is very perfect and has been applied to commercial products widely, and the yield can achieve about 90%. However, this method would produce a plenty of byproducts, which not only increases the production cost, but leads to unstable product quality due to separation of byproducts; further, this process cannot implement continuous production as a result of factors, such as byproducts. The reaction principle is as follows:

Ethylene oxide method has some defects: a plenty of sulfuric acid and caustic soda liquid are used in the reaction. Sulfuric acid and base would be converted as sodium sulphate in the end; after a long time, sodium sulphate would take away one part of taurine, thereby leading to material loss; at the same time, sodium sulphate always exists in the mother liquid, so the residual sulphate would be left in the rough product when centrifugal separation is performed to produce rough taurine, and sulphate in the final product exceeds the standard easily. Further, a cooler, a heater, a synthesis reactor or a high-pressure pipe may be blocked easily under the high-temperature and high-pressure synthesis condition, and production cannot be implemented normally because the mother liquid includes sulphate. At the same time, a plenty of solid sulphate waste would increase the labor strength and cannot be handled easily. ② As one-time extraction rate is limited due to existence of sodium sulphate after neutral reaction, taurine ($H_2NCH_2CH_2SO_3H$) should be extracted for multiple times during the subsequent extraction process, thereby generating a plenty of waste mother liquid, leading to waste of raw material and low yield, and causing environmental pollution; at the same time, a plenty of vapor is consumed when concentrating the mother liquid, thereby leading to high energy consumption. A plenty of waste solid sodium sulphate is generated, which causes great pressure to environmental protection.

In order to obtain taurine from sodium taurate, U.S. Pat. No. 2,693,488 claims a method using ion exchange resin. A H-type strong acidic cation exchange resin is used first, and then an alkali anion exchange resin is used. This process is complicated; and in each production circulation, a plenty of acid and base are required during regeneration of the ion exchange resin.

On the other hand, Chinese patents CN101508657, CN10158658, CN10158659 and CN101486669 describe a method of obtaining taurine and sodium sulphate from sulfuric acid and sodium taurate through neutral reaction. Rough taurine can be obtained easily by filtering a crystal suspension after cooling. However, the waste mother liquor still includes taurine, ammonium sulphate and other organic impurities.

To sum up, although it is relatively mature, the existing taurine preparation process still has many defects in aspects of separation and purification of taurine, recycling use of intermediate byproducts or resourceful treatment, and one effective method is in badly need to overcome these defects.

BRIEF SUMMARY OF THE INVENTION

The invention discloses a high-yield circular production method of taurine, aiming to overcome defects in existing taurine preparation process to a certain extent.

The invention disclosures a technical solution of solving the above-mentioned technical problems as follows: a high-yield circular production method of taurine including following steps:

S1, ethylene oxide reacts with sodium bisulfite solution to generate sodium hydroxyethyl sulfonate;

S2, sodium hydroxyethyl sulfonate obtained in S1 is mixed with ammonia to obtain a reaction solution; ammonolysis reaction is implemented in presence of a catalyst; excessive ammonia is discharged from the reaction solution through flash evaporation upon completion of reaction and recycled as raw material of ammonolysis reaction;

S3, the reaction solution obtained after flash evaporation in S2 is sent to pass through an acidic cation exchange resin column at constant speed; the pH of liquid discharged from a collecting opening at lower end of the acidic cation exchange resin column is monitored; the liquid discharged is collected from the moment when the pH increases until the pH is more than 10, wherein the discharged liquid collected is the material liquid containing taurine; the material is not fed any longer when the material liquid is not collected; then an acidic cation resin is subjected to regeneration with sulfur dioxide or carbon dioxide aqueous solution for recycling; and a regenerative eluent acquired during regeneration can be recycled as the raw material of S1 directly or recycled after treated by sulfur dioxide;

S4, the material liquid collected in S3 is subjected to concentration and crystallization, separation and purification and drying to acquire solid taurine.

What needs illustration is that the sulfur dioxide aqueous solution also includes sodium sulfite and sodium bisulfite, etc. besides sulfur dioxide and sulfurous acid, namely the carbon dioxide aqueous solution can be obtained by introducing sulfur dioxide with regenerated eluent as solvent instead of dissolving sulfur dioxide with pure water as solvent. The process, on one hand, can save water effectively, and can increase concentration of sodium bisulfite in the regenerated eluent during circular regeneration on the other hand; in this way, the regenerated eluent is more suitable to be used as raw material in S1. Similarly, the carbon dioxide aqueous solution also includes sodium carbonate and sodium bicarbonate besides carbon dioxide and carbonic acid, namely corresponding regenerated eluent (sodium bicarbonate solution or sodium carbonate solution) can also be selected as the solvent for dissolving carbon dioxide.

The sodium hydroxyethyl sulfonate generated in S1 can be subjected to concentration and crystallization and dried to obtain corresponding solid or the untreated mixed liquid after reaction is mixed with ammonia in S2 directly to obtain corresponding reaction solution, wherein the concentration of ammonia is 20-28 wt %.

On the basis of the above-mentioned technical solution, the invention can be further specified or optimized as follows.

Specifically, the concentration of sodium bisulfite solution in S1 is 9-36 wt %; and the mass ratio of sodium bisulfite to ethylene oxide is 1:(0.95-1).

Specifically, the catalyst in S2 is any one or a mixture of any two or more selected form sodium hydroxide, potassium hydroxide, lithium hydroxide, sodium carbonate, potassium carbonate and lithium carbonate; and the ammonolysis reaction is implemented at 150-280° C. in presence of pressure being 10-25 MPa.

Specifically, the regeneration of the acidic cation resin with sulfur dioxide aqueous solution in S3 is implemented under protection of nitrogen or carbon dioxide in order to prevent acidic cation resin from formation of corresponding sulfate as a result of oxidation due to oxygen in the air during regeneration; the regenerated eluent is sodium bisulfite or sodium sulfite solution (in fact, sodium bisulfite solution or sodium sulfite solution here includes two solutes—sodium bisulfite or sodium sulfite generally) and can be recycled directly as the raw material of S1; the regenerated eluent is sodium bicarbonate or sodium carbonate solution (similar to the condition in the above-mentioned bracket) during regeneration of the acidic cation resin with the carbon dioxide aqueous solution in S3, and is changed as sodium bisulfite solution when treated by sulfur dioxide; then the regenerated eluent is recycled as the raw material of S1.

Specifically, the flow rate of reaction solution in S3 is at 0.25-2.5 BV/h when passing through the acidic cation resin column. Preferably, the flow rate is controlled at 0.8-1.2 BV/h.

Specifically, the pH of the material liquid collected in S3 and containing taurine is 4-9. The pH of the material liquid collected can be monitored while monitoring pH of the liquid discharged from the collecting opening of the resin column. One or both of two pH values are taken as the criterion of starting and ending of material liquid collection and criterion of regenerating the resin column and stopping feeding.

Specifically, the method of monitoring pH of the liquid discharged from the collecting opening in S3 is sampling detection or online detection; and the liquid discharged from the collecting opening is subjected to pH sampling detection once when 0.08-0.15 BV material liquid is collected every time. Preferably, online detection of pH is selected, with higher efficiency, labor saving and significant industrialization characteristics.

Specifically, the flow rate of the sulfur dioxide aqueous solution or carbon dioxide aqueous solution passing through the acidic cation resin column is 1.8-2.2 BV/h when regeneration for acidic cation resin is implemented with sulfur dioxide aqueous solution or carbon dioxide aqueous solution in S3; 2-3 BV sulfur dioxide aqueous solution or carbon dioxide aqueous solution is used; the regenerated eluent is collected when 1 BV material is discharged during regeneration; then the acidic cation resin column is washed with de-ionized water until the pH is 4.8-5.2 for later use.

Specifically, the acidic cation exchange resin is carboxylic acid type cation exchange resin or sulfonic acid type cation exchange resin; when sulfur dioxide solution is selected to implement regeneration, the acidity of the acidic cation exchange resin selected is the intermediate value between sulphurous acid and taurine; and when carbon dioxide solution is selected to implement regeneration, the acidity of the acidic cation exchange resin selected is the intermediate value between carbonic acid and taurine.

Specifically, concentration and crystallization, separation and purification and drying in S4 specifically include following contents: the material liquid collected in S3 is subjected to concentration and crystallization and centrifuged successively; the mother liquid after centrifugation is recycled as a solvent of ammonolysis reaction; rough taurine obtained after centrifugation is recrystallized and separated after decolourization; the concentrated mother liquid after separation is mixed with the material liquid collected in next batch; and refined taurine obtained after separation is dried to obtain solid taurine. What needs illustration is that the rough and refined taurine separation device is one of a suction filter, a filter or intermittent centrifugal separator, and a continuous liquid-solid separator, including but not limited to a continuous settling separator, hydraulic cyclone separator, continuous filter separator, and continuous centrifugal separator.

Compared with the prior art, the invention has following beneficial effects:

The acidity of the acidic cation exchange resin selected in the invention is the intermediate value between sulfur dioxide aqueous solution (sulfurous acid) and taurine, or between carbon dioxide aqueous solution (carbonic acid) and taurine; therefore, the reaction solution passing through the acidic cation exchange resin and containing sodium taurate is converted as the taurine material liquid. The acidic cation exchange resin can be regenerated through sulfur dioxide aqueous solution or carbon dioxide aqueous solution when inactivated after exchanging too many sodium ions; and the regenerated eluent produced during regeneration and containing sodium bisulfite or sodium bicarbonate (which is changed as sodium bisulfite after absorbing sulfur dioxide) can be recycled directly or after treatment for addition reaction with ethylene oxide. Further, ammonia obtained through flash evaporation after ammonolysis reaction can be recycled; the mother liquid or concentrated mother liquid separated during concentration and crystallization and recrystallization can also be recycled or recycled for re-purification. The whole process generates a little waste liquid; and part of substances during the process is recycled effectively, thereby saving cost. Further, the yield of taurine can achieve 90% and above; at the same time, the production process is relatively simple and can be put into mass production easily.

DETAILED DESCRIPTION OF THE INVENTION

In the following further explains the specific contents of the invention by combining the figures and specific embodiments; and the embodiments shall be used for explaining the invention rather than limiting the scope of the invention.

Figure 1:
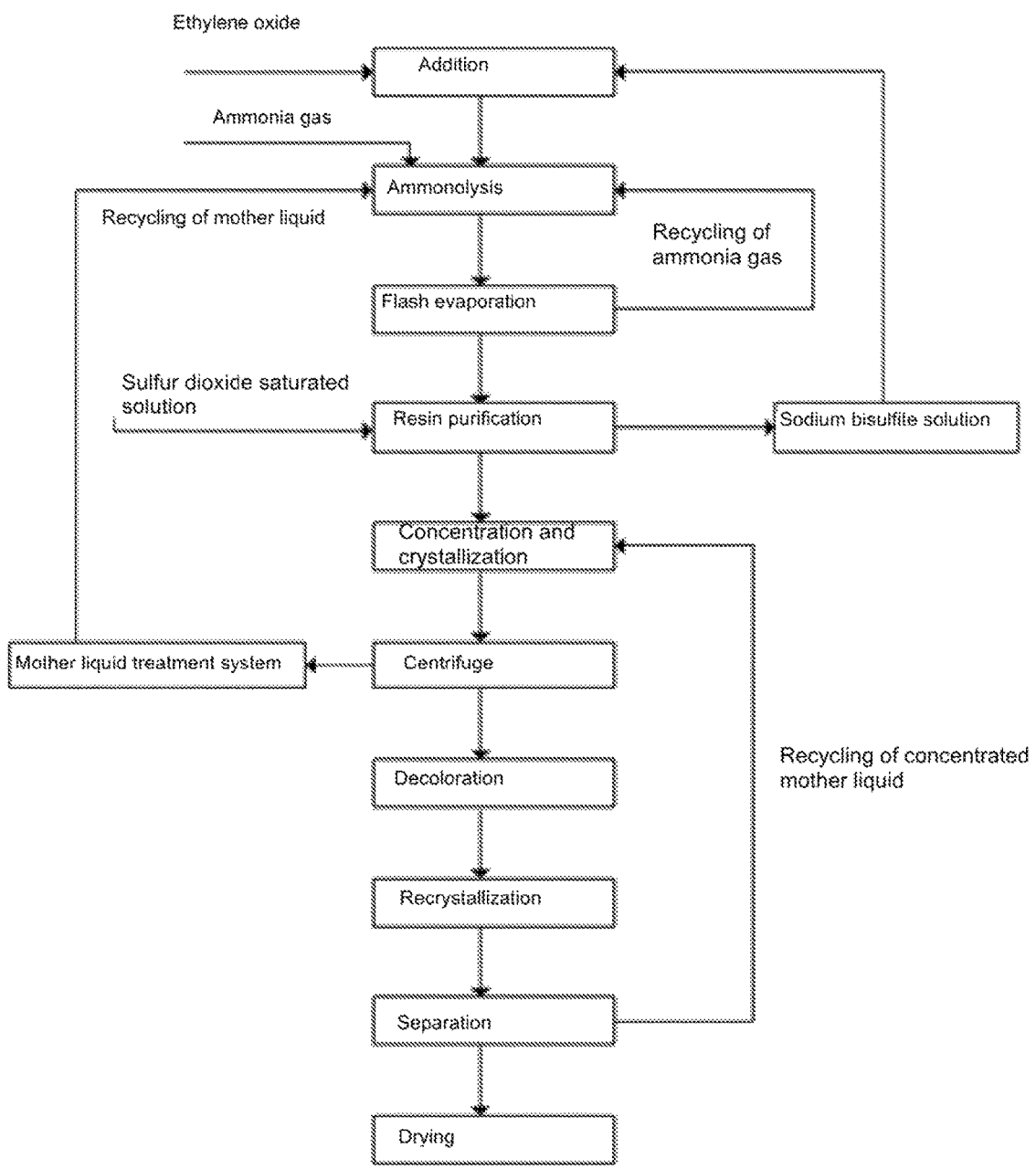
FIG. 1 is a process flow diagram of a high-yield circular production method of taurine (regenerating a resin column with sulfur dioxide aqueous solution) provided in the invention.
Figure 2:
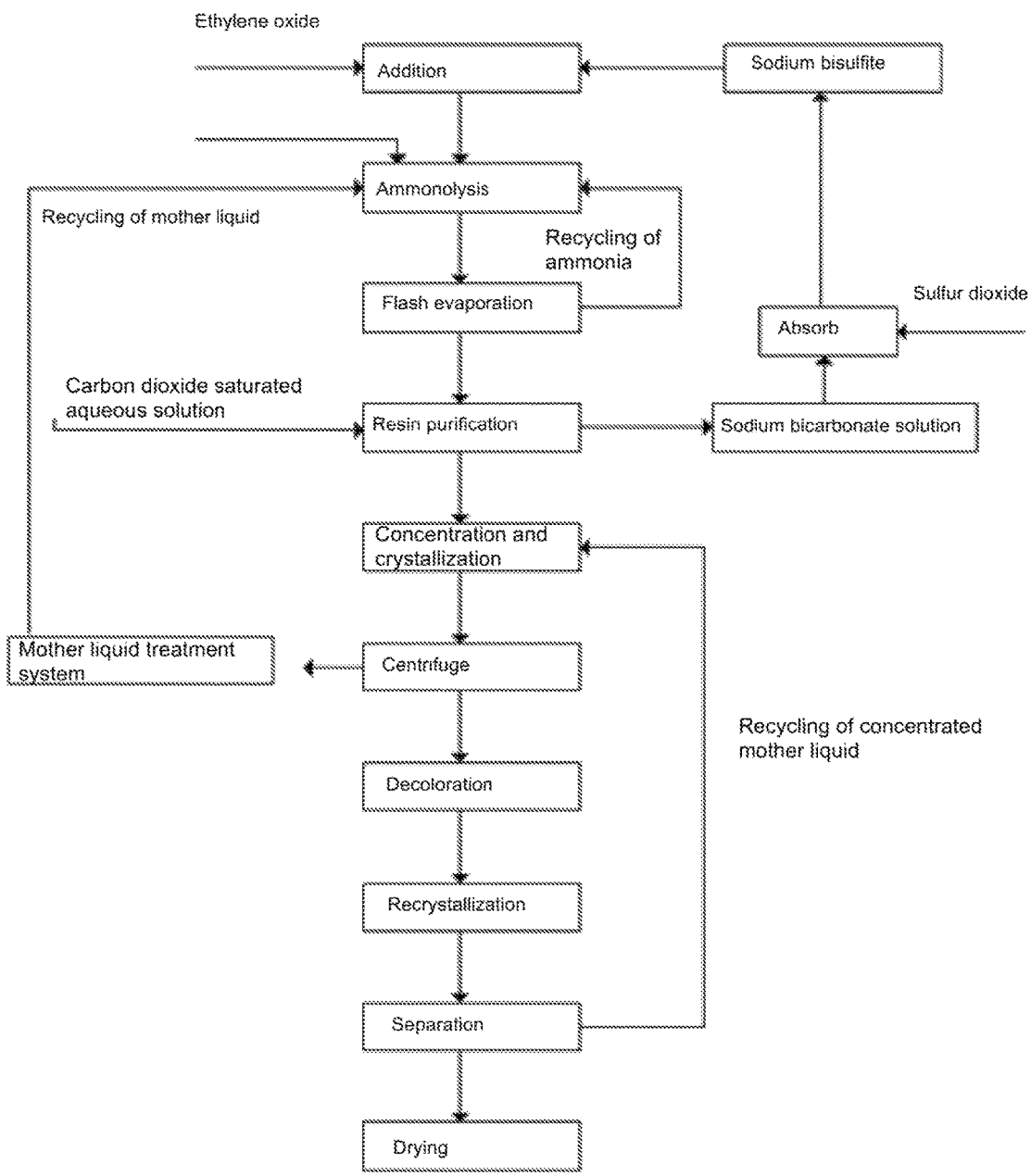
FIG. 2 is a process flow diagram of another high-yield circular production method of taurine (regenerating a resin column with carbon dioxide aqueous solution) provided in the invention.

As shown in FIG. 1 and FIG. 2, the invention discloses a high-yield circular production method of taurine, including following steps:

S1, ethylene oxide reacts with sodium bisulfite solution to generate sodium hydroxyethyl sulfonate;

S2, sodium hydroxyethyl sulfonate obtained in S1 is mixed with ammonia to obtain a reaction solution; ammonolysis reaction is implemented in presence of a catalyst; excessive ammonia is discharged from the reaction solution through flash evaporation upon completion of reaction and recycled as raw material of ammonolysis reaction;

S3, the reaction solution obtained after flash evaporation in S2 is sent to pass through an acidic cation exchange resin column at constant speed; the pH of liquid discharged from a collecting opening at lower end of the acidic cation exchange resin column is monitored; the liquid discharged is collected from the moment when the pH increases until the pH is more than 10, wherein the discharged liquid collected is the material liquid containing taurine; the material is not fed any longer when the material liquid is not collected; then an acidic cation resin is subjected to regeneration with sulfur dioxide or carbon dioxide aqueous solution for recycling; and a regenerative eluent acquired during regeneration can be recycled as the raw material of S1 directly or recycled after treated by sulfur dioxide;

S4, the material liquid collected in S3 is subjected to concentration and crystallization, separation and purification and drying to acquire solid taurine.

It's understandable that the high-yield circular production method of taurine can be implemented discontinuously, semi-continuously or continuously. Further, the regeneration with sulfur dioxide solution in the invention shall be implemented under protection of nitrogen or carbon dioxide in order to prevent sodium bisulfite in the material from influence when used as raw material of S1 after deterioration due to conversion as sodium sulphate. If carbon dioxide solution is applied to elution and regeneration, protection of nitrogen is not required because elution and regeneration are usually implemented in the open condition; while conversion of sodium bicarbonate solution into sodium bisulfite solution by charging sulfur dioxide is usually implemented in the closed condition because oxidative deterioration would take place less likely and there are many methods to avoid its oxidation.

The steps in the high-yield circular production method of taurine provided by the invention are decomposed in following embodiments, and each embodiment is taken as one step of the method or part of contents in one step. The drug used in following embodiments, unless otherwise specifically stated, shall be sold in the market; and the methods to be used shall be the conventional method unless otherwise specifically stated; and content of material, unless otherwise specifically stated, shall be mass percent in volume.

Embodiment 1

Pre-treatment (or regeneration) of acidic cation exchange resin column is shown in this embodiment:

When starting pre-treatment, a carboxylic acid type cation exchange resin is packed into an exchange column with wet method; 2 BV saturated sulphur dioxide aqueous solution passes through the resin in the exchange column positively at flow rate of 1.8-2.2 BV/h (any value) under protection of nitrogen; then the resin is washed with the de-ionized water until the pH thereof is equal to 5 for later use. The resin is packed into a measuring cylinder with wet method when packed into the column. A 5-10 cm aqueous layer is ensured at the upper layer of the resin. The measuring cylinder is shaken slightly to compact the resin; then the resin is transferred into the exchange column with wet method, wherein a 5-10 cm aqueous layer is reserved at the upper part of a resin layer; and no bubble is allowable in the resin layer.

During regeneration, no resin is packed into the column, but water is directly added to remove the material in the resin column; then 2 BV saturated sulphur dioxide aqueous solution passes through the resin in the exchange column positively at flow rate of 2 BV/h. When 1 BV material is discharged, regenerated eluent shall be collected and washed with de-ionized water until the pH thereof is equal to 5 to complete regeneration. The washing water can be mixed with the regenerated eluent; and eluent obtained after the regenerated eluent is mixed with the washing water can be applied to addition reaction with ethylene oxide as raw material containing sodium bisulfite.

During regeneration, the saturated carbon dioxide solution can be used instead of saturated sulfur dioxide solution to complete regeneration of the resin column smoothly; however, the saturated carbon dioxide solution used is 3-4 BV, and the regeneration time is significantly longer. Further, protection from nitrogen is not required during regeneration, and regeneration can be operated more easily.

Besides the carboxylic acid type cation exchange resin, sulfonic acid type cation exchange resin can also be used to obtain corresponding resin column.

Embodiment 2

Treatment of sodium taurate solution with carboxylic acid type cation exchange resin column subjected to pre-treatment or regeneration in Embodiment 1 is shown in this embodiment:

1250 ml sodium taurate aqueous solution with mass percent in volume of 10% (namely, 100 mL solution includes 10 g taurine on the basis of taurine) is taken to pass through the resin column positively at flow rate of 0.25-2.5 BV/h (any value); and the water in the resin layer discharged at the outlet primarily is not required to collect (discharge of material liquid can be judged by detecting pH; and when the pH is changed, the material liquid flows outwards). The material liquid is metered and collected when flowing outwards; the sample is taken to detect pH every 0.08-0.15 BV (any value). When an index of the material liquid at an outlet is consistent with that at an inlet basically (namely pH values are close to each other), feeding of material is stopped. The material liquid is leached out and recycled with de-ionized water flowing positively at flow rate of 2 BV/h; and the material is collected, wherein the total volume is about 1850 ml; the content of taurine is 6.7%; and the pH of the material liquid is about 7.0 (during actual production in factory, the leaching-out step of the material liquid is implemented only when the resin is required to regenerate). When the material is removed completely, 2 BV saturated sulphur dioxide aqueous solution is taken to pass through the resin layer positively at flow rate of 2 BV/h; when 1 BV material is discharged, the regenerated eluent is collected and washed with the de-ionized water until the pH thereof is equal to 5 for later use. This washing water can be mixed with the regenerated eluent to obtain about 900 mL recycled liquid mainly including sodium bisulfite. Through detection, the recycled liquid contains 11% sodium bisulfite (which can be recycled as the raw material to participate in reaction with ethylene oxide or converted as the saturated sulphur dioxide aqueous solution by charging sulphur dioxide for regeneration of the resin column).

Embodiment 3

Concentration and crystallization, separation and purification and drying of material liquid are shown in this embodiment:

The collected material with total volume of about 1850 mL contains 6.7% taurine through detection; the material is concentrated, cooled to 20° C. to be crystallized and then subjected to centrifugal separation to obtain 125 g rough product with mass content of 92.5%; and the rough product also includes 7% of water. The rest mother liquid is 72 mL, with content of 11.56%. Then 125 g rough product is subjected to decolorization, recrystallization, separation and drying to obtain the 81 g refined dry product and 345 mL concentrated mother liquid (with content of 10%). Detected data of the refined product is as follows:

| Item | Standard | Measured data |
| --- | --- | --- |
| Description: | White crystal, crystalline powder or spherical particle, and tartish taste without odor | White crystalline powder, and tartish taste without odor |

-continued

| Item | Standard | Measured data |
| --- | --- | --- |
| Particle size: | Pass 10-mesh analysis sieve completely | Be in line with the standard |
| Content ($C_2H_7NSO_3$): | 98.5-101.5% | 99.6% |
| Clarity of solution: | ≤0.5# turbidity standard | Be in line with the standard |
| Readily carbonizable substance: | The solution shall be colorless. | The solution is colorless. |
| Chloride: | ≤0.01% | <0.01% |
| Sulphate: | ≤0.01% | <0.01% |
| Ammonium salt: | ≤0.02% | <0.02% |
| Residue on ignition: | ≤0.1% | 0.05% |
| Loss on drying: | ≤0.2% | 0.10% |
| Heavy metal (on the basis of Pb): | ≤0.001% | <0.001% |
| Arsenic salt (on the basis of As): | ≤0.0002% | <0.0002% |

Recycling of sodium bisulfite solution (900 mL recycled liquid in Embodiment 2) and recycling of mother liquid (72 mL mother liquid in Embodiment 3) are shown in this embodiment.

Preparation of sodium hydroxyethyl sulfonate: the sodium bisulfite solution collected in Embodiment 2 reacts with ethylene oxide for 1 h when the pressure is 0.1 Mpa, pH is 6.0-7.0 and the temperature is at 70-85° C. to prepare sodium hydroxyethyl sulfonate, wherein the molar ratio of sodium bisulfite to ethylene oxide is 1:(0.95-1).

Preparation of sodium taurate: sodium hydroxyethyl sulfonate is ammonolyzed with the mother liquid collected in Embodiment 3 and ammonia for 1 h in presence of a catalyst—sodium hydroxide when the temperature is at 250-270° C. and the pressure is 10-15 MPa; after reaction, ammonia is removed through flash evaporation to obtain the solution, namely sodium taurate solution.

The above-mentioned contents just involve the better embodiments of the invention only and are not to limit the invention. Any modification, equivalent replacement, improvement, etc. within the spirit and principle of the invention shall belong to the scope of protection of the invention.

We claim:

1. A high-yield circular production method of taurine, comprising the steps of:
    S1, reacting ethylene oxide with sodium bisulfite solution to generate sodium hydroxyethyl sulfonate;
    S2, mixing the sodium hydroxyethyl sulfonate obtained in S1 with ammonia to obtain a reaction solution, wherein an ammonolysis reaction is implemented in presence of a catalyst and wherein excessive ammonia is discharged from the reaction solution through flash evaporation upon completion of reaction and recycled as raw material of ammonolysis reaction;
    S3, sending the reaction solution obtained after flash evaporation in S2 to pass through an acidic cation exchange resin column at constant speed, wherein the pH of liquid discharged from a collecting opening at lower end of the acidic cation exchange resin column is monitored, wherein the liquid discharged is collected from the moment when the pH increases until the pH is more than 10, wherein the discharged liquid collected is the material liquid containing taurine, wherein the material is not fed any longer when the material liquid is not collected, wherein an acidic cation resin is subjected to regeneration with sulfur dioxide or carbon dioxide aqueous solution for recycling, and wherein a regenerative eluent acquired during regeneration can be recycled as the raw material of S1 directly or recycled after treated by sulfur dioxide; and S4, subjecting the material liquid collected in S3 to concentration and the concentrate is subjected to crystallization, separation and purification and drying to acquire solid taurine.

2. The high-yield circular production method of taurine, according to claim 1, wherein the concentration of sodium bisulfite solution in S1 is 9-36 wt %; and wherein the mass ratio of sodium bisulfite to ethylene oxide is 1:(0.95-1).

3. The high-yield circular production method of taurine, according to claim 1, wherein the catalyst in S2 is comprised of any one or a mixture of any two or more selected form sodium hydroxide, potassium hydroxide, lithium hydroxide, sodium carbonate, potassium carbonate and lithium carbonate; and wherein the ammonolysis reaction is implemented at 150-280° C. in presence of pressure being 10-25 MPa.

4. The high-yield circular production method of taurine, according to claim 1, wherein the regeneration of acidic cation resin with sulfur dioxide aqueous solution in S3 is implemented under protection of nitrogen or carbon dioxide in order to prevent acidic cation resin from formation of corresponding sulfate as a result of oxidation due to oxygen in the air during regeneration; the regenerated eluent is sodium bisulfite or sodium sulfite solution and can be recycled directly as the raw material of S1, and wherein the regenerated eluent is sodium bicarbonate or sodium carbonate solution during regeneration of the acidic cation resin with the carbon dioxide aqueous solution in S3, and is changed as sodium bisulfite solution when treated by sulfur dioxide; then the sodium bisulfite solution is recycled as the raw material of S1.

5. The high-yield circular production method of taurine, according to claim 1, wherein the flow rate of the reaction solution in S3 is at 0.25-2.5 BV/h when passing through the acidic cation resin column.

6. The high-yield circular production method of taurine, according to claim 1, wherein the pH of the material liquid collected in S3 and containing taurine is 4-9.

7. The high-yield circular production method of taurine, according to claim 1, wherein the method of monitoring pH of the liquid discharged from the collecting opening in S3 is sampling detection or online detection, and wherein the liquid discharged from the collecting opening is subjected to pH sampling detection once when 0.08-0.15 BV material liquid is collected every time.

8. The high-yield circular production method of taurine, according to claim 1, wherein the flow rate of the sulfur dioxide aqueous solution or carbon dioxide aqueous solution passing through the acidic cation resin column reaches 1.8-2.2 BV/h when regeneration of acidic cation resin is implemented with sulfur dioxide aqueous solution or carbon dioxide aqueous solution in S3, wherein 2-3 BV sulfur dioxide aqueous solution or carbon dioxide aqueous solution is used, and wherein the regenerated eluent is collected when 1 BV material is discharged during regeneration; then the acidic cation resin column is washed with de-ionized water until the pH is 4.8-5.2 for later use.

9. The high-yield circular production method of taurine, according to claim 1, wherein the acidic cation exchange resin is carboxylic acid type cation exchange resin or sulfonic acid type cation exchange resin, wherein, when sulfur dioxide solution is selected to implement regeneration, the acidity of the acidic cation exchange resin selected is the intermediate value between sulphurous acid and taurine, and wherein, when carbon dioxide solution is selected to implement regeneration, the acidity of the acidic cation exchange resin selected is the intermediate value between carbonic acid and taurine.

10. The high-yield circular production method of taurine, according to claim 1, wherein concentration and crystallization, separation and purification and drying in S4 specifically comprises following steps: the material liquid collected in S3 is concentrated and crystallized and then centrifuged; the mother liquid acquired after centrifugation is recycled as a solvent of ammonolysis reaction; rough taurine obtained after centrifugation is recrystallized and separated after decolourization; the concentrated mother liquid after separation is mixed with the material liquid collected in next batch; and the taurine obtained after separation is dried to obtain the solid taurine.

11. The high-yield circular production method of taurine, according to claim 1, wherein the sulfur dioxide aqueous solution comprises sodium sulfite and sodium bisulfite besides sulfur dioxide and sulfurous acid, namely the sulfur dioxide aqueous solution can be obtained by introducing sulfur dioxide with the regenerated eluent as solvent.

12. The high-yield circular production method of taurine, according to claim 1, wherein the carbon dioxide aqueous solution comprises sodium carbonate and sodium bicarbonate besides carbon dioxide and carbonic acid, namely the carbon dioxide aqueous solution can be obtained by introducing carbon dioxide with the regenerated eluent as solvent.

13. The high-yield circular production method of taurine, according to claim 1, wherein the sodium hydroxyethyl sulfonate which is mixed with ammonia in S2 to obtain the reaction solution is solid sodium hydroxyethyl sulfonate acquired through purification and drying after reaction in S1 or untreated liquid mixture containing sodium hydroxyethyl sulfonate after reaction in S1; and its concentration of ammonia is 20-28 wt %.

* * * * *